US010568964B2

(12) United States Patent
Yamaguchi et al.

(10) Patent No.: US 10,568,964 B2
(45) Date of Patent: Feb. 25, 2020

(54) NEUTRON CAPTURE THERAPY SYSTEM AND THERAPY PLANNING SYSTEM FOR NEUTRON CAPTURE THERAPY (71) Applicants: SUMITOMO HEAVY INDUSTRIES, LTD., Tokyo (JP); KYOTO UNIVERSITY, Kyoto (JP)

(72) Inventors: Takashi Yamaguchi, Kanagawa (JP); Tetsuya Mukawa, Kanagawa (JP); Hiroki Tanaka, Kyoto (JP)

(73) Assignees: SUMITOMO HEAVY INDUSTRIES, LTD., Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/358,136

(22) Filed: Mar. 19, 2019

(65) Prior Publication Data
US 2019/0209687 A1 Jul. 11, 2019

Related U.S. Application Data (63) Continuation of application No. PCT/JP2017/033135, filed on Sep. 13, 2017.

(30) Foreign Application Priority Data

Sep. 23, 2016 (JP) ................. 2016-185797

(51) Int. Cl.
*A61K 41/00* (2020.01)
*A61N 5/10* (2006.01)
(52) U.S. Cl.
CPC ........ *A61K 41/0095* (2013.01); *A61N 5/1031* (2013.01); *A61N 5/1049* (2013.01);
(Continued)

(58) Field of Classification Search
CPC .............. A61K 41/0095; A61N 5/1049; A61N 5/1031; A61N 2005/109; A61N 2005/1072; A61N 5/1077; A61N 2005/1095
(Continued)

(56) References Cited

U.S. PATENT DOCUMENTS 7,576,344 B2 * 8/2009 Ein-Gal ............... A61B 6/0414
250/492.1
8,180,020 B2 5/2012 Kilby et al.
(Continued)

FOREIGN PATENT DOCUMENTS

EP 2 878 338 A1 6/2015
JP 2005-512028 A 4/2005
(Continued)

OTHER PUBLICATIONS

International Search Report issued in Application No. PCT/JP2017/033135, dated Oct. 10, 2017.
(Continued)

*Primary Examiner* — Michael Maskell
(74) *Attorney, Agent, or Firm* — Michael Best & Friedrich LLP (57) ABSTRACT

A neutron capture therapy system includes a therapy table on which an irradiation target is placed, a neutron beam irradiation unit which irradiates the irradiation target placed on the therapy table with a neutron beam, a position measurement unit which measures a position of the irradiation target placed on the therapy table, and a radiation dose distribution output unit which outputs a radiation dose distribution of a neutron beam used for irradiating the irradiation target, based on an amount of positional misalignment of the position of the irradiation target measured by the position measurement unit.

2 Claims, 8 Drawing Sheets (52) U.S. Cl.
CPC ...... *A61N 5/1077* (2013.01); *A61N 2005/109* (2013.01); *A61N 2005/1059* (2013.01); *A61N 2005/1061* (2013.01); *A61N 2005/1072* (2013.01); *A61N 2005/1095* (2013.01)

(58) Field of Classification Search
USPC ................................ 250/491.1, 492.1–492.3
See application file for complete search history.

(56) References Cited

U.S. PATENT DOCUMENTS

| | | | |
|---|---|---|---|
| 9,044,602 | B2 | 6/2015 | Kilby et al. |
| 9,895,556 | B2 | 2/2018 | Bharat |
| 2003/0125616 | A1 | 7/2003 | Black et al. |
| 2010/0317968 | A1* | 12/2010 | Wright ............... A61B 5/06 600/427 |
| 2011/0006212 | A1* | 1/2011 | Shchory ............. A61N 5/1049 250/363.01 |

FOREIGN PATENT DOCUMENTS

| | | |
|---|---|---|
| JP | 2006-043235 A | 2/2006 |
| JP | 2008-302129 A | 12/2008 |
| JP | 2009-213709 A | 9/2009 |
| JP | 2012-506724 A | 3/2012 |
| JP | 2014-190754 A | 10/2014 |
| JP | 2014-195505 A | 10/2014 |
| JP | 2015-524304 A | 8/2015 |
| JP | 2015-231497 A | 12/2015 |

OTHER PUBLICATIONS

Fredriksson et al., "Optimizing the Scenario Positions for Robust Radiation Therapy Treatment Planning," Department of Mathematics, Royal Institute of Technology, XP055215222, https://people.kth.se/~andersf/doc/scenariooptimization.pdf, Oct. 10, 2012.
Search report issued in European Application No. 17852923.6, dated Aug. 26, 2019.

* cited by examiner

| No. | PARALLEL MOVEMENT (mm) | | | ROTATION (°) | | |
|---|---|---|---|---|---|---|
| | $\delta X$ | $\delta Y$ | $\delta Z$ | $\delta \theta$ | $\delta \phi$ | $\delta \psi$ |
| 1 | -5 | -5 | -5 | -5 | -5 | -5 |
| 2 | 0 | -5 | -5 | -5 | -5 | -5 |
| 3 | 5 | -5 | -5 | -5 | -5 | -5 |
| 4 | -5 | 0 | -5 | -5 | -5 | -5 |
| 5 | 0 | 0 | -5 | -5 | -5 | -5 |
| 6 | 5 | 0 | -5 | -5 | -5 | -5 |
| 7 | -5 | 5 | -5 | -5 | -5 | -5 |
| 8 | 0 | 5 | -5 | -5 | -5 | -5 |
| 9 | 5 | 5 | -5 | -5 | -5 | -5 |
| 10 | -5 | -5 | 0 | -5 | -5 | -5 |
| 11 | 0 | -5 | 0 | -5 | -5 | -5 |
| 12 | 5 | -5 | 0 | -5 | -5 | -5 |
| 13 | -5 | 0 | 0 | -5 | -5 | -5 |
| 14 | 0 | 0 | 0 | -5 | -5 | -5 |
| 15 | 5 | 0 | 0 | -5 | -5 | -5 |
| 16 | -5 | 5 | 0 | -5 | -5 | -5 |
| 17 | 0 | 5 | 0 | -5 | -5 | -5 |
| 18 | 5 | 5 | 0 | -5 | -5 | -5 |
| 19 | -5 | -5 | 5 | -5 | -5 | -5 |
| 20 | 0 | -5 | 5 | -5 | -5 | -5 |
| 21 | 5 | -5 | 5 | -5 | -5 | -5 |
| 22 | -5 | 0 | 5 | -5 | -5 | -5 |
| 23 | 0 | 0 | 5 | -5 | -5 | -5 |
| 24 | 5 | 0 | 5 | -5 | -5 | -5 |
| 25 | -5 | 5 | 5 | -5 | -5 | -5 |
| 26 | 0 | 5 | 5 | -5 | -5 | -5 |
| 27 | 5 | 5 | 5 | -5 | -5 | -5 |
| 28 | -5 | -5 | -5 | 0 | 0 | 0 |
| 29 | 0 | -5 | -5 | 0 | 0 | 0 |
| 30 | 5 | -5 | -5 | 0 | 0 | 0 |
| 31 | -5 | 0 | -5 | 0 | 0 | 0 |
| 32 | 0 | 0 | -5 | 0 | 0 | 0 |
| 33 | 5 | 0 | -5 | 0 | 0 | 0 |
| 34 | -5 | 5 | -5 | 0 | 0 | 0 |
| 35 | 0 | 5 | -5 | 0 | 0 | 0 |
| 36 | 5 | 5 | -5 | 0 | 0 | 0 |
| 37 | -5 | -5 | 0 | 0 | 0 | 0 |
| 38 | 0 | -5 | 0 | 0 | 0 | 0 |
| 39 | 5 | -5 | 0 | 0 | 0 | 0 |
| 40 | -5 | 0 | 0 | 0 | 0 | 0 |
| 41 | 0 | 0 | 0 | 0 | 0 | 0 |

FIG. 8

| No. | PARALLEL MOVEMENT (mm) | | | ROTATION (°) | | |
|---|---|---|---|---|---|---|
| | δX | δY | δZ | δθ | δφ | δψ |
| 42 | 5 | 0 | 0 | 0 | 0 | 0 |
| 43 | -5 | 5 | 0 | 0 | 0 | 0 |
| 44 | 0 | 5 | 0 | 0 | 0 | 0 |
| 45 | 5 | 5 | 0 | 0 | 0 | 0 |
| 46 | -5 | -5 | 5 | 0 | 0 | 0 |
| 47 | 0 | -5 | 5 | 0 | 0 | 0 |
| 48 | 5 | -5 | 5 | 0 | 0 | 0 |
| 49 | -5 | 0 | 5 | 0 | 0 | 0 |
| 50 | 0 | 0 | 5 | 0 | 0 | 0 |
| 51 | 5 | 0 | 5 | 0 | 0 | 0 |
| 52 | -5 | 5 | 5 | 0 | 0 | 0 |
| 53 | 0 | 5 | 5 | 0 | 0 | 0 |
| 54 | 5 | 5 | 5 | 0 | 0 | 0 |
| 55 | -5 | -5 | -5 | 5 | 5 | 5 |
| 56 | 0 | -5 | -5 | 5 | 5 | 5 |
| 57 | 5 | -5 | -5 | 5 | 5 | 5 |
| 58 | -5 | 0 | -5 | 5 | 5 | 5 |
| 59 | 0 | 0 | -5 | 5 | 5 | 5 |
| 60 | 5 | 0 | -5 | 5 | 5 | 5 |
| 61 | -5 | 5 | -5 | 5 | 5 | 5 |
| 62 | 0 | 5 | -5 | 5 | 5 | 5 |
| 63 | 5 | 5 | -5 | 5 | 5 | 5 |
| 64 | -5 | -5 | 0 | 5 | 5 | 5 |
| 65 | 0 | -5 | 0 | 5 | 5 | 5 |
| 66 | 5 | -5 | 0 | 5 | 5 | 5 |
| 67 | -5 | 0 | 0 | 5 | 5 | 5 |
| 68 | 0 | 0 | 0 | 5 | 5 | 5 |
| 69 | 5 | 0 | 0 | 5 | 5 | 5 |
| 70 | -5 | 5 | 0 | 5 | 5 | 5 |
| 71 | 0 | 5 | 0 | 5 | 5 | 5 |
| 72 | 5 | 5 | 0 | 5 | 5 | 5 |
| 73 | -5 | -5 | 5 | 5 | 5 | 5 |
| 74 | 0 | -5 | 5 | 5 | 5 | 5 |
| 75 | 5 | -5 | 5 | 5 | 5 | 5 |
| 76 | -5 | 0 | 5 | 5 | 5 | 5 |
| 77 | 0 | 0 | 5 | 5 | 5 | 5 |
| 78 | 5 | 0 | 5 | 5 | 5 | 5 |
| 79 | -5 | 5 | 5 | 5 | 5 | 5 |
| 80 | 0 | 5 | 5 | 5 | 5 | 5 |
| 81 | 5 | 5 | 5 | 5 | 5 | 5 | ion computation unit computes the radiation dose distribution regarding a plurality of patterns achieved by causing a position of the irradiation target to be misaligned from a reference position by amounts respectively set in advance.

NEUTRON CAPTURE THERAPY SYSTEM AND THERAPY PLANNING SYSTEM FOR NEUTRON CAPTURE THERAPY

RELATED APPLICATIONS

Priority is claimed to Japanese Patent Application No. 2016-185797, filed Sep. 23, 2016, and International Patent Application No. PCT/JP2017/033135, the entire content of each of which is incorporated herein by reference.

BACKGROUND

Technical Field

A certain embodiment of the present invention relates to a neutron capture therapy system and a therapy planning system for neutron capture therapy.

Description of Related Art

As a therapeutic method using radial rays, boron neutron capture therapy (BNCT), which is neutron capture therapy irradiating cancer cells with a neutron beam and annihilates the cancer cells, is known. In boron neutron capture therapy, boron that has been injected into cancer cells in advance is irradiated with a neutron beam so that the cancer cells are selectively destroyed due to dispersion of heavy charged particles generated through the irradiation. In such neutron capture therapy, generally, a patient placed on a therapy table is irradiated with a neutron beam (for example, refer to the related art).

In such neutron capture therapy described above, there are cases where a patient moves during irradiation of radial rays resulting in misalignment of an irradiation position. Therefore, there has been a demand for a neutron capture therapy system capable of performing proper therapy even when an irradiation position is misaligned.

It is desirable to provide a neutron capture therapy system capable of performing proper therapy in consideration of misalignment of an irradiation position, and a therapy planning system for neutron capture therapy.

SUMMARY

According to an embodiment of the invention, there is provided a neutron capture therapy system including a therapy table on which an irradiation target is placed, a neutron beam irradiation unit which irradiates the irradiation target placed on the therapy table with a neutron beam, a position measurement unit which measures a position of the irradiation target placed on the therapy table, and a radiation dose distribution output unit which outputs a radiation dose distribution of a neutron beam used for irradiating the irradiation target, based on an amount of positional misalignment of the position of the irradiation target measured by the position measurement unit.

In addition, according to another embodiment of the invention, there is provided a therapy planning system for neutron capture therapy performing therapy planning for neutron capture therapy in which an irradiation target is irradiated with a neutron beam. The therapy planning system for neutron capture therapy includes an irradiation condition setting unit which sets an irradiation condition; a radiation dose distribution computation unit which computes a radiation dose distribution estimated to be used for irradiating the irradiation target, based on the irradiation condition set by the irradiation condition setting unit; and an output unit which outputs a result computed by the radiation dose distribution computation unit. The radiation dose distribu-

DETAILED DESCRIPTION

According to the neutron capture therapy system, the position measurement unit can measure the position of the irradiation target placed on the therapy table. In addition, the radiation dose distribution output unit outputs a radiation dose distribution of a neutron beam used for irradiating the irradiation target, based on the amount of positional misalignment of the position of the irradiation target measured by the position measurement unit. Accordingly, the radiation dose distribution output unit can output a radiation dose distribution in consideration of misalignment of an irradiation position. Consequently, proper therapy can be performed in consideration of misalignment of an irradiation position.

The neutron capture therapy system may further include a storage unit in which the radiation dose distribution of a neutron beam corresponding to the amount of positional misalignment is stored in advance for each amount of positional misalignment of the irradiation target placed on the therapy table. The radiation dose distribution output unit may acquire the radiation dose distribution of a neutron beam used for irradiating the irradiation target, from the storage unit. Since data of positional misalignment estimated in advance is stored, the radiation dose distribution output unit can promptly output the radiation dose distribution in consideration of misalignment of an irradiation position.

According to the therapy planning system for neutron capture therapy, the radiation dose distribution computation unit can compute a radiation dose distribution estimated to be used for irradiating an irradiation target, regarding a plurality of patterns achieved by causing a position of the irradiation target to be misaligned from a reference position by amounts respectively set in advance. Accordingly, proper therapy planning can be established in consideration of misalignment of an irradiation position during irradiation. In addition, proper therapy can be performed in consideration of misalignment of an irradiation position by performing therapy based on such therapy planning.

Hereinafter, a therapy planning system for neutron capture therapy according to an embodiment of the invention, and a neutron capture therapy system including the same will be described with reference to the accompanying drawings. In each diagram, the same reference signs are applied to parts which are the same or corresponding, and duplicated description will be omitted.

Figure 1:
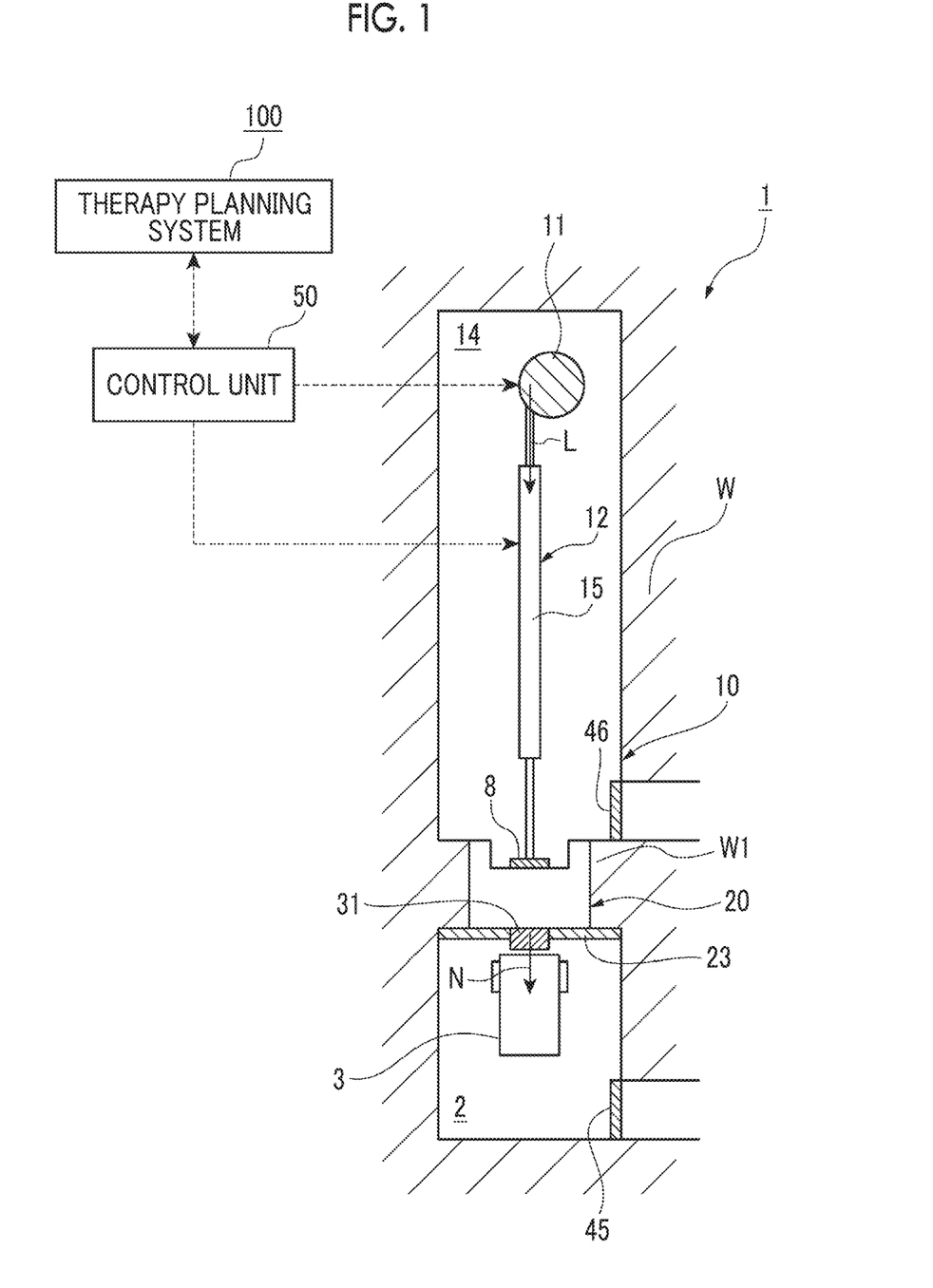
FIG. 1 is a view illustrating a configuration of a neutron capture therapy system of the present embodiment.
Figure 2:
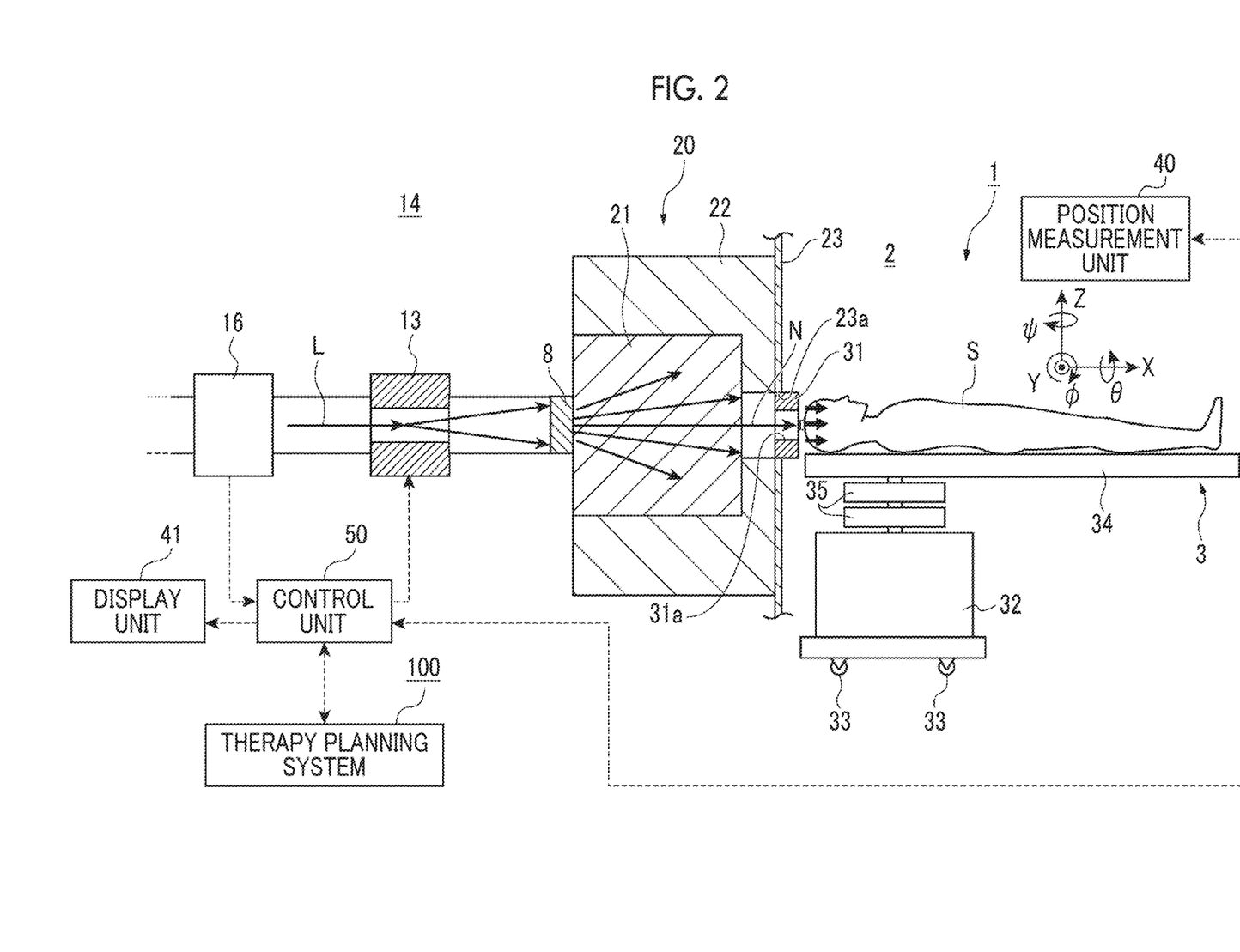
FIG. 2 is a view illustrating a part in the vicinity of a neutron beam irradiation unit in the neutron capture therapy system in FIG. 1.

First, using FIGS. 1 and 2, an overview of the neutron capture therapy system according to the present embodiment will be described. As illustrated in FIGS. 1 and 2, a neutron capture therapy system 1 for performing cancer therapy using a method of boron neutron capture therapy is a system in which cancer therapy is performed by irradiating a site of a patient S (irradiation target), to which a medicine including boron (10B) is applied such that the boron is clustered, with a neutron beam. The neutron capture therapy system 1 has an irradiation chamber 2 in which cancer therapy of the patient S bound to a therapy table 3 is performed by irradiating the patient S with a neutron beam N.

Preparation work in which the patient S is bound to the therapy table 3 is carried out in a preparation room (not illustrated) outside the irradiation chamber 2, and the therapy table 3, to which the patient S is bound, is moved from the preparation room to the irradiation chamber 2. In addition, the neutron capture therapy system 1 includes the therapy table 3 on which the patient S is placed, a neutron beam generation unit 10 which generates the neutron beam N for therapy, a neutron beam irradiation unit 20 which irradiates the patient S placed on the therapy table 3 inside the irradiation chamber 2 with the neutron beam N, a position measurement unit 40 which measures a position of the patient S placed on the therapy table 3, a control unit 50 which operates as a radiation dose distribution output unit outputting a radiation dose distribution of the neutron beam N used for irradiating the patient S, based on an amount of positional misalignment of the position of the patient S measured by the position measurement unit 40, a display unit 41 which displays information output from the control unit 50, and a therapy planning system. 100 which will be described below. The irradiation chamber 2 is covered with a blockade wall W. A passage and a door 45 through which a patient, a worker, or the like passes are provided.

Here, the amount of positional misalignment denotes an amount of misalignment of the position (posture) of the patient S actually measured by the position measurement unit 40 from a reference position. In the following description, the reference position indicates a posture of a patient determined as the most proper posture when therapy is performed by the therapy planning system 100. However, the reference position is not limited thereto, and it can be set in any desired manner as long as the position can be referred to when positional misalignment is computed or measured. The amount of positional misalignment may be indicated by using movement components and rotational components in three-dimensional directions or may be indicated by using only one composition thereof.

The neutron beam generation unit 10 includes an acceleration unit 11 which accelerates charged particles and causes a charged particle beam L to exit, a beam transportation path 12 through which the charged particle beam L caused to exit by the acceleration unit 11 is transported, a charged particle beam scanning unit 13 which controls the irradiation position of the charged particle beam L with respect to a target 8 by performing scanning with the charged particle beam L, the target 8 which causes nuclear reaction to irradiation of the charged particle beam L and generates the neutron beam N, and a current monitor 16 which measures a current of the charged particle beam L. The acceleration unit 11 and the beam transportation path 12 are disposed inside a charged particle beam generation chamber 14 having a substantially rectangular shape, and this charged particle beam generation chamber 14 is a space covered with the blockade wall W made of concrete. A passage and a door 46 through which a worker passes for maintenance are provided in the charged particle beam generation chamber 14. The shape of the charged particle beam generation chamber 14 is not limited to a substantially rectangular shape. The charged particle beam generation chamber 14 may have a different shape. For example, in a case where a route from the acceleration unit to a target has an L-shape, the charged particle beam generation chamber 14 may also have an L-shape. In addition, for example, the charged particle beam scanning unit 13 controls the irradiation position of the charged particle beam L with respect to the target 8, and the current monitor 16 measures the current of the charged particle beam L with which the target 8 is irradiated.

The acceleration unit 11 accelerates charged particles such as protons and generates the charged particle beam L such as a proton beam. In the present embodiment, a cyclotron is employed as the acceleration unit 11. As the acceleration unit 11, a different acceleration unit such as a synchrotron, a synchro-cyclotron, or a linear accelerator may be used instead of the cyclotron.

One end (end portion on the upstream side) of the beam transportation path 12 is connected to the acceleration unit 11. The beam transportation path 12 includes a beam adjustment unit 15 that adjusts the charged particle beam L. The beam adjustment unit 15 has a horizontal steering electromagnet and a horizontal-vertical steering electromagnet for adjusting the axis of the charged particle beam L, and a quadrupole electromagnet for restraining radiation of the charged particle beam L, a four-way slit for shaping the charged particle beam L, and the like. The beam transportation path 12 need only have a function of transporting the charged particle beam L, and the beam adjustment unit 15 is not essential.

The irradiation position of the charged particle beam L transported through the beam transportation path 12 is controlled by the charged particle beam scanning unit 13, and the target 8 is irradiated with the charged particle beam L. The charged particle beam scanning unit 13 may be omitted, such that the same place in the target 8 is irradiated with the charged particle beam L at all times.

The target 8 generates the neutron beam N in response to irradiation of the charged particle beam L. For example, the target 8 is formed of beryllium (Be), lithium (Li), tantalum (Ta), or tungsten (W) in a plate shape. However, the target is not limited to having a plate shape and may be in a liquefied state or the like. The neutron beam irradiation unit 20 irradiates the patient S inside the irradiation chamber 2 with the neutron beam N generated by the target 8.

The neutron beam irradiation unit 20 includes a moderator 21 that decelerates the neutron beam N which has exited from the target 8, and a beam blockage body 22 that blocks the neutron beam N and radial rays such as gamma rays from being radiated to the outside. The moderator 21 and the beam blockage body 22 constitute a moderator.

For example, the moderator 21 has a laminated structure formed of a plurality of different materials, and the material of the moderator 21 can be suitably selected depending on various conditions, such as energy, of the charged particle beam L. Specifically, for example, in a case where the acceleration unit 11 outputs a proton beam of 30 MeV and a beryllium target is used as the target 8, lead, iron, aluminum, or calcium fluoride can be adopted as the material of the moderator 21.

The beam blockage body 22 is provided to surround the moderator 21 and has a function of blocking the neutron beam N and radial rays such as gamma rays caused in response to the generated neutron beam N from being radiated to the outside of the beam blockage body 22. At least a part of the beam blockage body 22 may be embedded in a wall W1 separating the charged particle beam generation chamber 14 and the irradiation chamber 2 from each other, or the beam blockage body 22 does not have to be embedded therein. In addition, a wall body 23 forming a part of a side wall surface of the irradiation chamber 2 is provided between the irradiation chamber 2 and the beam blockage body 22. A collimator attachment portion 23a serving as an output port for the neutron beam N is provided in the wall body 23. A collimator 31 for regulating the irradiation field of the neutron beam N is fixed to this collimator attachment portion 23a. The collimator 31 may be attached to the therapy table 3 (which will be described below), without providing the collimator attachment portion 23a in the wall body 23.

In the neutron beam irradiation unit 20 described above, the target 8 is irradiated with the charged particle beam L, and the target 8 generates the neutron beam N in response thereto. The neutron beam N generated by the target 8 is decelerated while passing through the inside of the moderator 21, and the neutron beam N, which has exited from the moderator 21, passes through the collimator 31, so that the patient S placed on the therapy table 3 is irradiated with the neutron beam N. Here, a thermal neutron beam or an epithermal neutron beam having comparatively low energy can be used as the neutron beam N.

The therapy table 3 functions as a placement table on which a patient is placed in neutron capture therapy and the therapy table 3 can be moved from the preparation room (not illustrated) to the irradiation chamber 2 while having the patient S placed thereon. The therapy table 3 includes a base unit 32 which constitutes a base of the therapy table 3, casters 33 which enable the base unit 32 to move on a floor surface, a top plate 34 on which the patient S is placed, and a driver 35 which causes the top plate 34 to relatively move with respect to the base unit 32. The base unit 32 may be fixed to the floor without using the casters 33.

The position measurement unit 40 measures the position of the patient S placed on the therapy table 3 and transmits the amount of positional misalignment with respect to the reference position of the patient S to the control unit 50, which will be described below. That is, the position measurement unit 40 determines that there is no positional misalignment (the amount of positional misalignment is zero) when the patient S has not moved from the posture of the patient acquired from the therapy planning system 100 (which will be described below). The position measurement unit 40 may obtain the amount of positional misalignment by measuring the position of the patient S after irradiation of a neutron beam ends or may be configured to continuously measure the position during irradiation of a neutron beam. In addition, the position measurement unit 40 may transmit positional information to the control unit 50, and the control unit 50 may calculate the amount of positional misalignment.

Figure 3A:
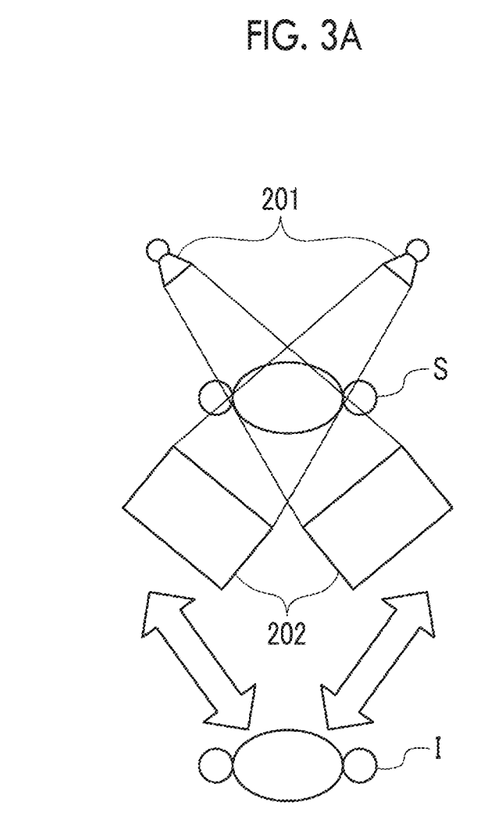
FIG. 3A is a view illustrating a position measurement unit using an X-ray transmission image.
Figure 3B:
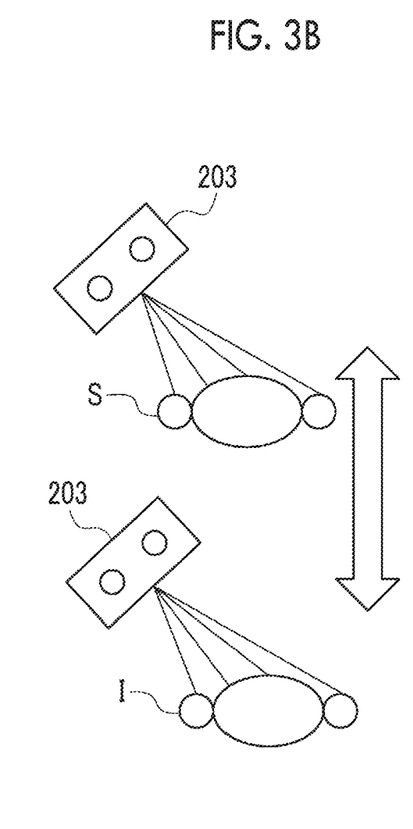
FIG. 3B is a view illustrating the position measurement unit using an infrared sensor.
Figure 3C:
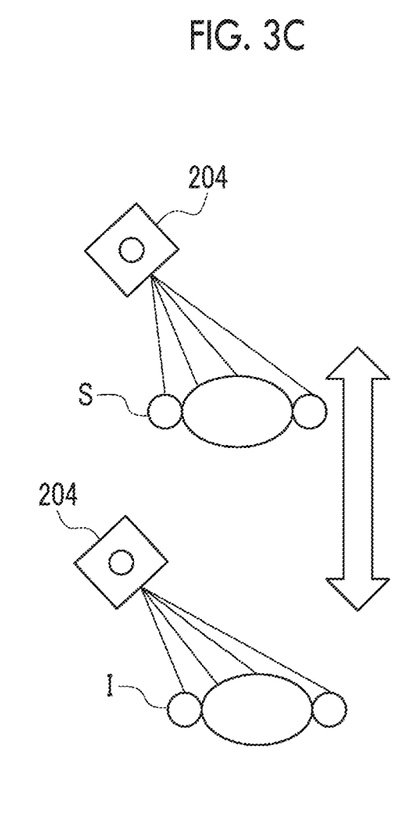
FIG. 3C is a view illustrating the position measurement unit using a camera.

As illustrated in FIGS. 3A to 3C, examples of the position measurement unit 40 include a method of using an X-ray transmission image, a method of using an infrared sensor, and a method of using an image captured by an optical camera. In the method illustrated in FIG. 3A, the amount of positional misalignment is measured by using an X-ray tube 201 and a detector 202 to capture an X-ray transmission image of the patient S and matching the X-ray transmission image with a CT image I for therapy planning. In the method illustrated in FIG. 3B, the amount of positional misalignment is measured by detecting the distance to a sampling position of the patient S using an infrared sensor 203 and comparing the sampling position with the position in the CT image I for therapy planning. In the method illustrated in FIG. 3C, the amount of positional misalignment is measured by detecting the body surface from an image of the patient S captured by an optical camera 204 and comparing the body surface with that in the CT image I for therapy planning.

The control unit 50 performs various kinds of control processing of the neutron capture therapy system 1. For example, the control unit 50 is constituted of a CPU, a ROM, and a RAM. The control unit 50 is electrically connected to the acceleration unit 11, the beam adjustment unit 15, the charged particle beam scanning unit 13, the current monitor 16, and the position measurement unit 40. In addition, the control unit 50 is electrically connected to the therapy planning system 100. The therapy planning system 100 performs therapy planning for neutron capture therapy irradiating the patient S with neutrons. The therapy planning system 100 outputs data related to therapy planning to the control unit 50. Consequently, the control unit 50 controls the acceleration unit 11, the beam adjustment unit 15, and the charged particle beam scanning unit 13 based on therapy planning output from the therapy planning system 100 and a detection result output from the current monitor 16.

Moreover, the control unit 50 operates as the radiation dose distribution output unit which outputs a radiation dose distribution of the neutron beam N used for irradiating the patient S, based on the amount of positional misalignment with respect to the reference position of the patient S measured by the position measurement unit 40. Specifically, in a storage unit 104 inside the therapy planning system 100 (which will be described below), the radiation dose distribution of a neutron beam used to irradiate the patient S at a position corresponding to the amount of positional misalignment is stored in advance for each amount of positional misalignment of the patient S placed on the therapy table 3. The control unit 50 acquires the radiation dose distribution corresponding to the position measured by the position measurement unit 40, from the storage unit 104.

Figure 4:
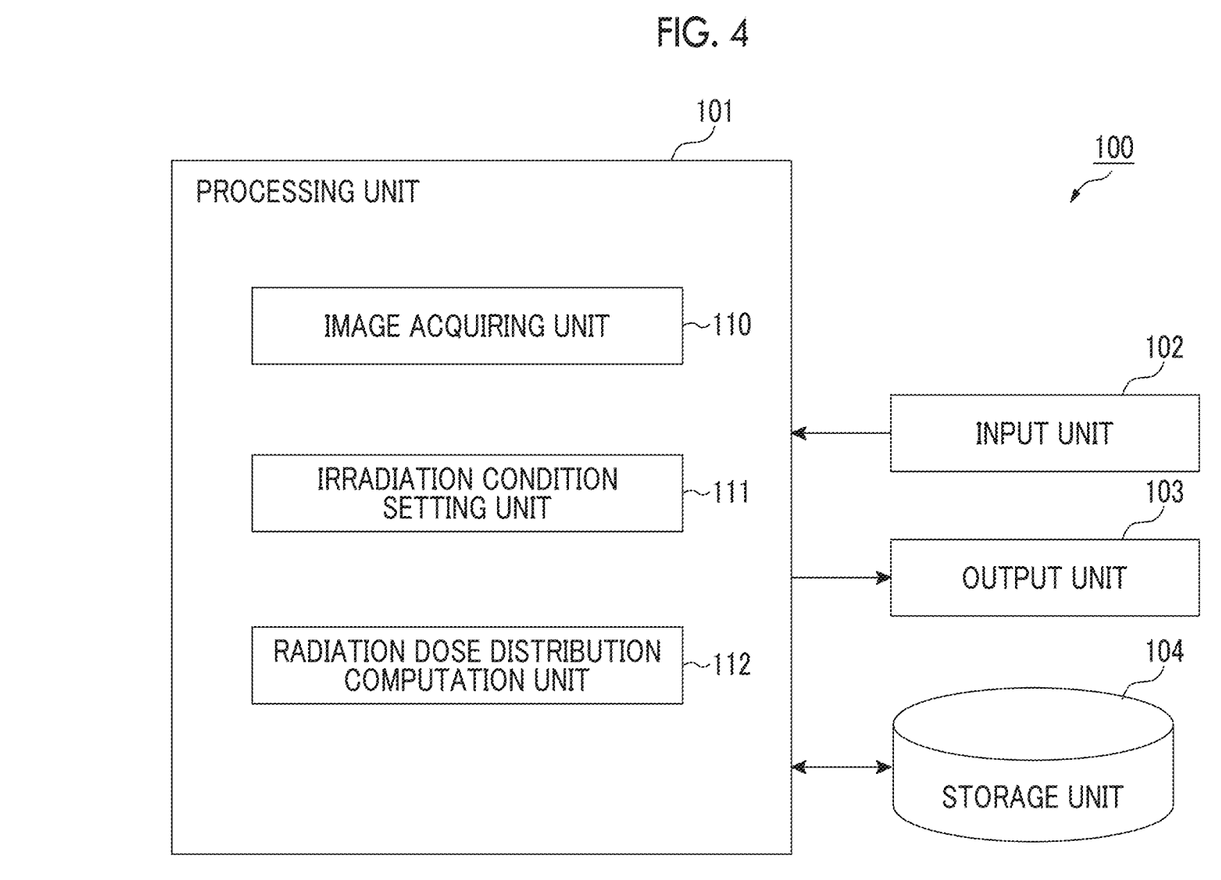
FIG. 4 is a block configuration diagram of a therapy planning system for neutron capture therapy in FIG. 1.

Subsequently, with reference to FIG. 4, a configuration of the therapy planning system 100 will be described in detail. FIG. 4 is a block configuration diagram illustrating a block configuration of the therapy planning system 100. The therapy planning system 100 includes a processing unit 101 that performs various kinds of information processing, an input unit 102 that is used by an operator to input various kinds of information, an output unit 103 that outputs various kinds of information for the operator, and a storage unit 104 that transmits and receives various kinds of information with respect to the processing unit 101. The input unit 102 is constituted of various kinds of interfaces, such as a keyboard and a mouse. The output unit 103 is constituted of a monitor or the like displaying various kinds of information from the processing unit 101. The storage unit 104 may store data of therapy planning or the like which stores CT images and is computed by the processing unit 101.

The processing unit 101 a function of performing various kinds of setting based on an image of the patient S and input information from the input unit 102 and computing the radiation dose distribution of a neutron beam and the like with respect to the patient S based on the setting information. Here, therapy of neutron capture therapy is a therapeutic method in which boron that has been injected into cancer cells in advance is irradiated with a neutron beam so that the cancer cells are selectively destroyed due to dispersion of heavy charged particles generated through nuclear reaction between the neutron beam and the boron. In this manner, since the therapy is a therapeutic method accompanying nuclear reaction, in order to grasp the radiation dose distribution in a scanned image of the patient S, the atomic composition of each region in the image of the patient S needs to be grasped. Therefore, the processing unit 101 sets regions in an image based on the atomic composition.

The processing unit 101 includes an image acquiring unit 110, an irradiation condition setting unit 111, and a radiation dose distribution computation unit 112.

The image acquiring unit 110 acquires an image of the patient S. The image acquiring unit 110 acquires the image by reading out the image stored in the storage unit 104. However, the image acquiring unit 110 may directly take an image from an external instrument. A CT image or the like is employed as an image to be acquired.

The irradiation condition setting unit 111 sets irradiation conditions such as the posture of the patient S, the irradiation position of the patient S to be irradiated (for example, isocentric coordinates), an irradiation angle, energy of irradiation particles, the diameter of a collimator, and the distance from the collimator to an isocenter, based on information input by an operator.

The radiation dose distribution computation unit 112 computes the radiation dose distribution of a neutron beam estimated to be used for irradiating the patient S, based on the irradiation conditions set by the irradiation condition setting unit 111. The result computed by the radiation dose distribution computation unit 112 is output by the output unit 103. Here, the radiation dose distribution computation unit 112 computes the radiation dose distribution estimated to be used for irradiating the patient S, regarding a plurality of patterns achieved by causing the position of the patient S to be misaligned from the reference position by amounts respectively set in advance. The plurality of patterns described above may be computed by the radiation dose distribution computation unit 112 based on the reference position set by the irradiation condition setting unit 111 or may be set by the irradiation condition setting unit 111.

Specifically, as illustrated in FIG. 2, XYZ coordinate axes with respect to the patient S are taken. Then, the plurality of patterns having parameters such as positional misalignment of parallel movement in X, Y, and Z-axis directions from the reference position, and the amount of positional misalignment due to rotation around each of the axes are set in advance. Here, the X-axis direction indicates an irradiation direction of a neutron beam (direction from the target 8 toward the collimator attachment portion 23a), the Y-axis direction indicates a direction perpendicular to the X-axis within a horizontal plane with respect to the ground, and the Z-axis direction indicates a direction perpendicular to the ground. In addition, the factor $\theta$ indicates a rotation angle around the X-axis, the factor $\phi$ indicates a rotation angle around the Y-axis, and the factor $\psi$ indicates a rotation angle around the Z-axis.

Figure 7:
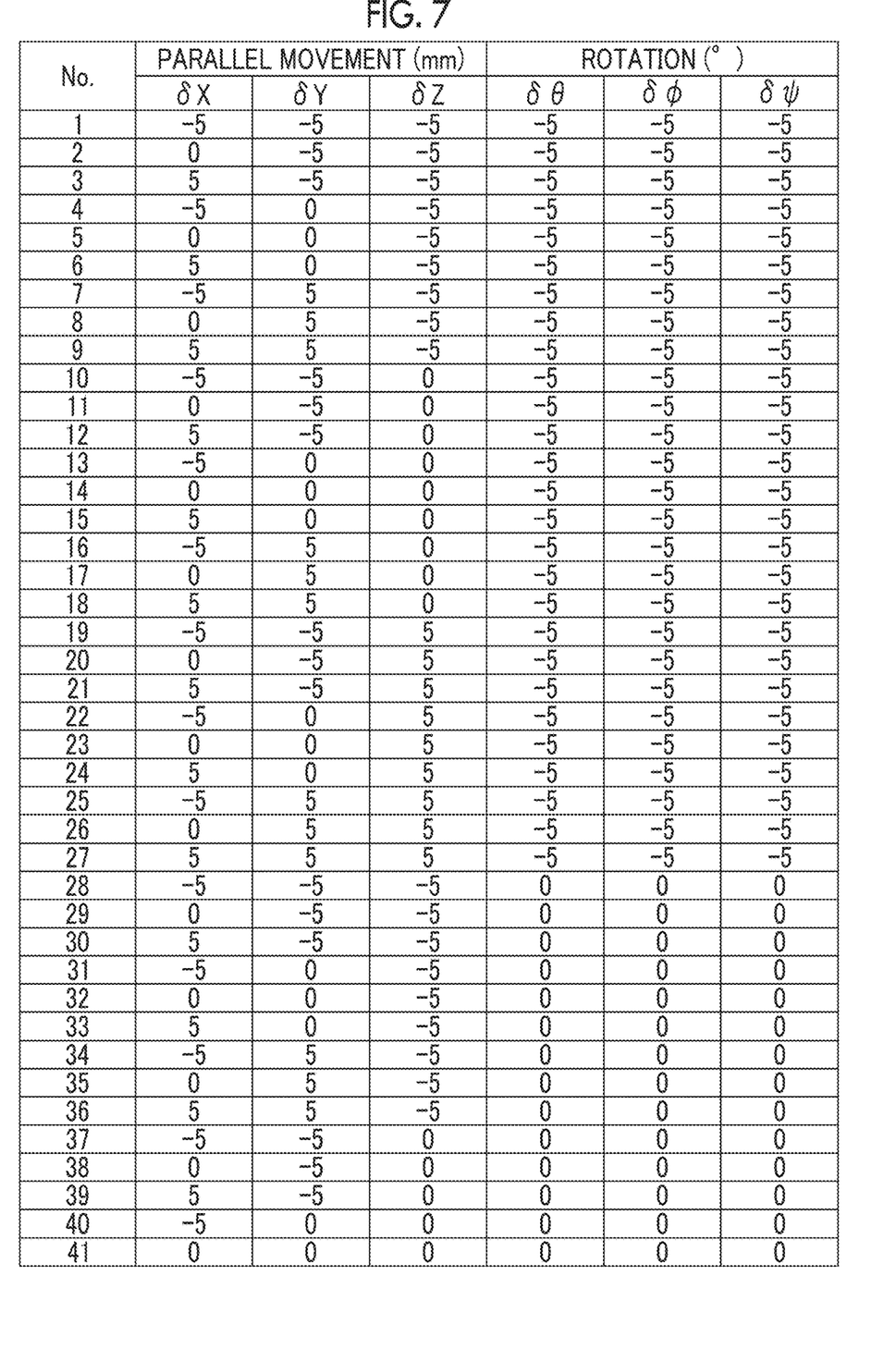
FIG. 7 is a table showing parametric values for an estimation pattern of positional misalignment.
Figure 8:
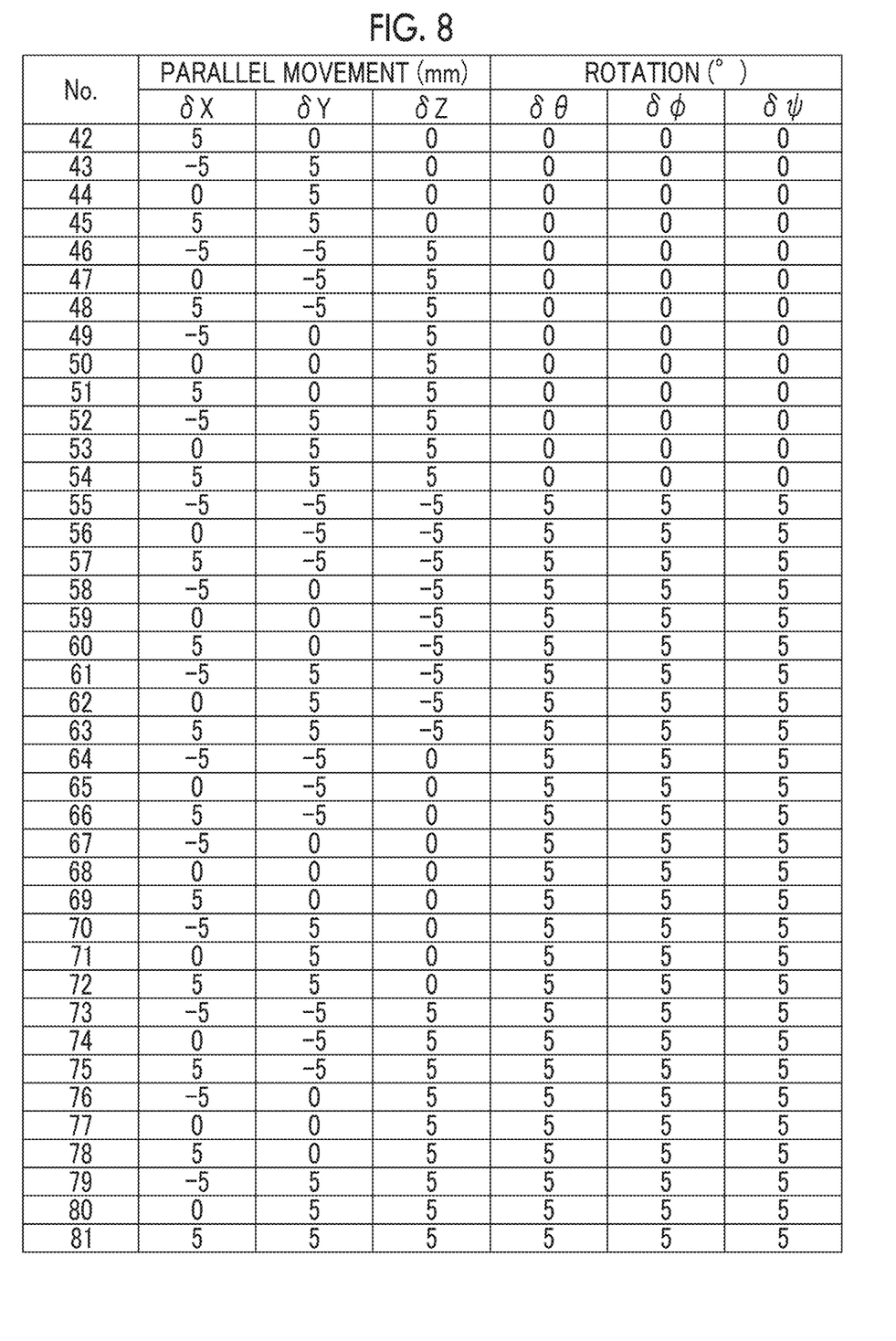
FIG. 8 is another table showing parametric values for the estimation pattern of positional misalignment.

FIGS. 7 and 8 show parametric values for estimation patterns of positional misalignment from No. 1 to No. 81 having a reference position of ($\delta X$, $\delta Y$, $\delta Z$, $\delta\theta$, $\delta\phi$, and $\delta\psi$)=(0, 0, 0, 0, 0, and 0). Each of these 81 patterns indicates a pattern when positional misalignment of parallel movement in the X-direction, the Y-direction, and the Z-direction is −5 mm, 0 mm, and 5 mm respectively, regarding three patterns in which the positional misalignment of $\theta$, $\phi$, and $\psi$ is −5°, 0°, and 5° respectively. The values of the parameters are not limited to the example described above. The values of the parameters may be able to be changed by an operator in any desired manner. It is necessary to keep in mind that if the number of patterns increases, the amount of computing radiation dose distribution increases. In such a case, regarding the pattern of positional misalignment, the computation time may be shortened by using a simple computation method.

Figure 5:
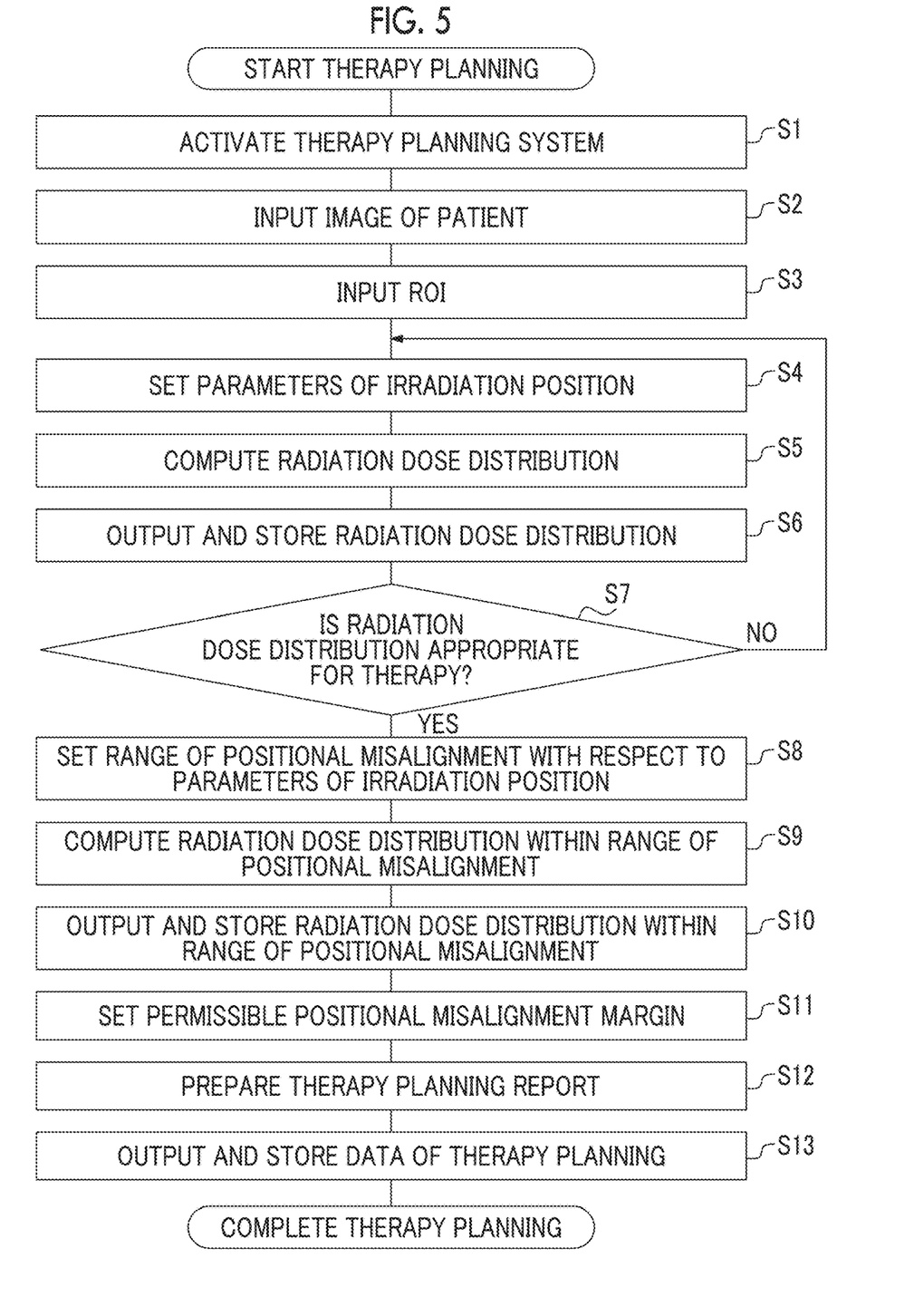
FIG. 5 is a flowchart illustrating a procedure of therapy planning.

Subsequently, with reference to FIG. 5, a procedure of therapy planning using the therapy planning system 100 will be described. In the following description, the processing performed by an operator indicates processing in which the therapy planning system 100 requests an input of information through the output unit 103 and an operator makes an input through the input unit 102 based on the request.

When therapy planning starts, the therapy planning system 100 is activated (Step S1).

When an image of a patient is input by an operator (Step S2), the processing unit 101 requests an input of a region of interest (ROI) of a neutron beam.

When the region of interest is input by the operator (Step S3), the irradiation condition setting unit 111 performs various kinds of setting for parameters of the irradiation position and the like based on the information input in Steps S2 and S3 (Step S4).

Subsequently, the radiation dose distribution computation unit 112 computes the radiation dose distribution in neutron capture therapy (Step S5). The computed radiation dose distribution is output by the output unit 103 and is stored in the storage unit 104 (Step S6). Accordingly, the operator can check the radiation dose distribution through the monitor or the like and can determine whether or not the output radiation dose distribution is appropriate.

Subsequently, determination whether or not the output radiation dose distribution is appropriate is set based on an input of the operator (Step S7). At this time, if an input indicating that the radiation dose distribution is appropriate is made, the processing proceeds to Step S8, and if an input indicating that the radiation dose distribution is insufficient is made the processing returns to Step S4.

if an input indicating that the radiation dose distribution is appropriate is made by the operator, the irradiation condition setting unit 111 sets the range of positional misalignment from the reference position with respect to the parameters of the irradiation position (Step S8).

Subsequently, the radiation dose distribution computation unit 112 computes the radiation dose distribution within the range of the positional misalignment set in Step S8 (Step S9). The computed radiation dose distribution is output by the output unit 103 and is stored in the storage unit 104 (Step S10). Accordingly, the operator can check the radiation dose distribution within the range of the positional misalignment through the monitor or the like and can determine a permissible positional misalignment margin.

Subsequently, the permissible positional misalignment margin is set based on an input of the operator (Step S11). The processing unit 101 prepares a therapy planning report based on this set margin (Step S12). The prepared therapy planning report is output by the output unit 103 and is stored in the storage unit 104 (Step S13). Through the procedure described above, therapy planning is completed.

The neutron capture therapy system 1 performs therapy of neutron capture therapy based on the therapy planning report described above and outputs a radiation dose distribution of a neutron beam used for actually irradiating the patient S based on the measurement results of the position measurement unit 40.

Figure 6:
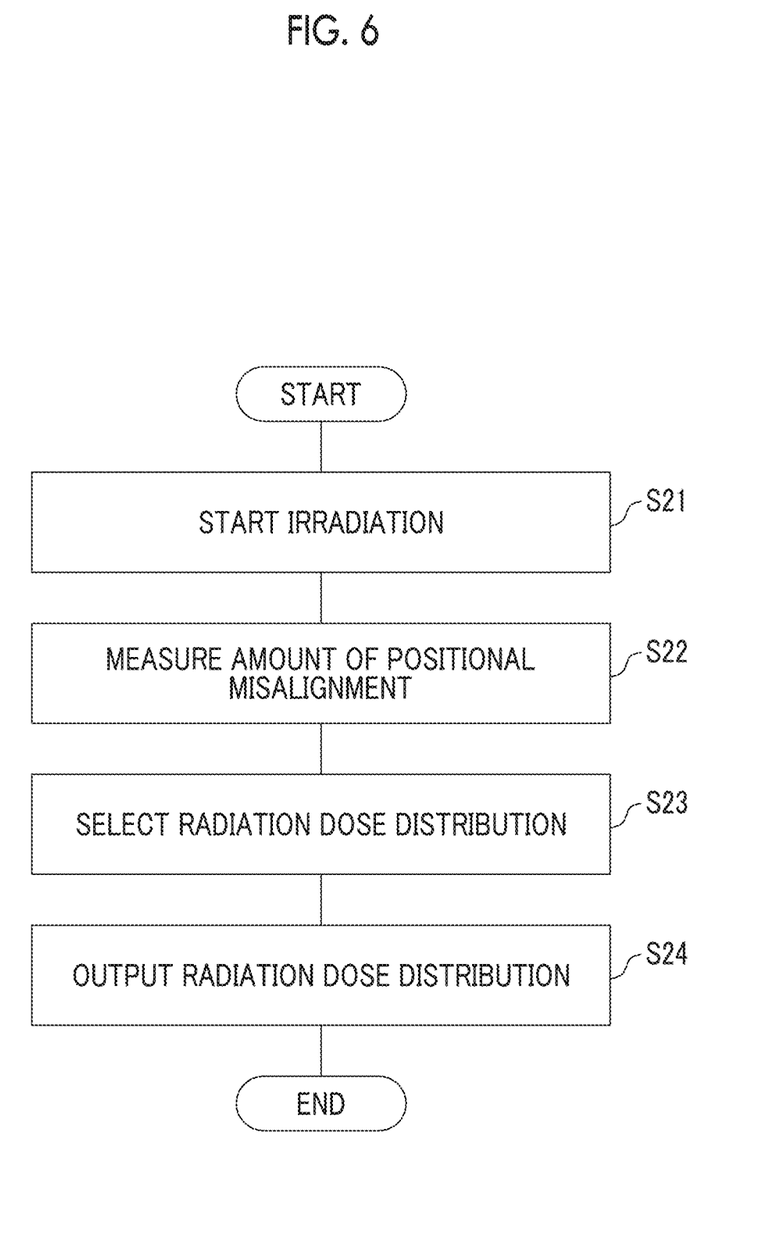
FIG. 6 is a flowchart illustrating a procedure of evaluating positional misalignment.

Hereinafter, with reference to FIG. 6, a procedure of outputting a radiation dose distribution in the neutron capture therapy system 1 performed in consideration of misalignment of an irradiation position will be described.

First, the control unit 50 starts irradiation of a neutron beam based on the therapy planning report prepared by the therapy planning system 100 (Step S21).

The control unit 50 causes the position measurement unit 40 to measure the amount of positional misalignment with respect to the reference position of the patient S after irradiation of a neutron beam ends (Step S22).

Subsequently, the control unit 50 reads data of the radiation dose distributions in the plurality of patterns having the amounts of positional misalignment as parameters from the storage unit 104 of the therapy planning system 100. Then, the control unit 50 selects a radiation dose distribution having a pattern closest to the amount of positional misalignment measured in Step S22 from the read data of the radiation dose distributions (Step S23).

The control unit 50 outputs the radiation dose distribution selected in Step S23 from the output unit 103, as the actual radiation dose distribution (Step S24). That is, the control unit 50 operates as a radiation dose distribution output unit which outputs a radiation dose distribution of a neutron beam used for irradiating the patient S, based on the amount of positional misalignment with respect to the reference position of the patient S measured by the position measurement unit 40.

Through the procedure described above, it is possible to output a radiation dose distribution in consideration of misalignment of an irradiation position.

Hereinafter, operations and effects of the neutron capture therapy system 1 according to the present embodiment will be described.

Incidentally, there are cases where a patient to be subjected to therapy of neutron capture therapy has to take a constrained posture for along time. Accordingly, there are cases where the posture of the patient changes during irradiation of a neutron beam, so that it is difficult to evaluate whether the radiation dose distribution with respect to the patient proceeds as the therapy planning.

In contrast, the neutron capture therapy system 1 according to the present embodiment includes the control unit 50 which outputs a radiation dose distribution of the neutron beam N used for irradiating the patient S, based on the amount of positional misalignment with respect to the reference position of the patient S. The control unit 50 outputs a radiation dose distribution of the neutron beam N used for irradiating the patient S, based on the amount of positional misalignment of the position of the irradiation target measured by the position measurement unit 40. Accordingly, the control unit 50 can output a radiation dose distribution in consideration of misalignment of an irradiation position. Thus, therapy of proper neutron capture therapy can be performed in consideration of misalignment of an irradiation position caused by changes in posture of a patient.

In addition, since data of estimated positional misalignment is stored in the storage unit 104 in advance, it is possible to promptly output a radiation dose distribution in consideration of misalignment of an irradiation position caused by changes in posture of a patient. In the case of performing multi-field irradiation, succeeding irradiation conditions can be set in consideration of insufficiency of the applied radiation dose by predicting an actual radiation dose distribution in this manner. In addition, even in the case of one field irradiation, it is possible to accumulate accurate data as therapeutic records.

In addition, according to the therapy planning system 100 in the present embodiment, it is possible to establish proper therapy planning in consideration of misalignment of an irradiation position caused by changes in posture of a patient during irradiation. Accordingly, it is possible to predict a permissible range of misalignment of an irradiation position in advance before irradiation of a neutron beam, so that it is possible to perform therapy of neutron capture therapy while taking an allowable range for movement into consideration.

Hereinabove, the embodiment of the invention has been described. However, the neutron capture therapy system and the therapy planning system for neutron capture therapy according to the present embodiment are not limited to those described above, and various changes can be made.

It should be understood that the invention is not limited to the above-described embodiment, but may be modified into various forms on the basis of the spirit of the invention. Additionally, the modifications are included in the scope of the invention.

What is claimed is:

1. A neutron capture therapy system comprising:
   a therapy table on which an irradiation target is placed;
   a neutron beam irradiation unit which irradiates the irradiation target placed on the therapy table with a neutron beam;
   a position measurement unit which measures a position of the irradiation target placed on the therapy table;
   a radiation dose distribution output unit which outputs a radiation dose distribution of a neutron beam used for irradiating the irradiation target after irradiation of the irradiation target with the neutron beam, based on an amount of positional misalignment of the position of the irradiation target measured by the position measurement unit; and
   a storage unit in which the radiation dose distribution of a neutron beam corresponding to the amount of positional misalignment is stored in advance for each amount of positional misalignment of the irradiation target placed on the therapy table,
   wherein the radiation dose distribution output unit acquires the radiation dose distribution of a neutron beam used for irradiating the irradiation target, from the storage unit,
   wherein the radiation dose distribution output unit obtains from the storage unit the radiation dose distribution of the neutron beam corresponding to the amount of positional misalignment of the position of the irradiation target measured by the position measurement unit and outputs the radiation dose distribution,
   wherein the storage unit stores radiation dose distributions regarding a plurality of patterns using the amount of positional misalignment as a parameter, and
   the radiation dose distribution output unit outputs a radiation dose distribution regarding a pattern closest to the amount of positional misalignment measured by the position measurement unit, among the radiation dose distributions regarding a plurality of patterns obtained from the storage unit.

2. The neutron capture therapy system according to claim 1, further comprising:

a monitor which displays the radiation dose distribution output from the radiation dose distribution output unit.

* * * * *